US00PP22896P2

(12) United States Plant Patent
Oudshoorn

(10) Patent No.: US PP22,896 P2
(45) Date of Patent: Jul. 24, 2012

(54) SEDUM PLANT NAMED 'ORANGE XENOX'

(50) Latin Name: *Hylotelephium spectabile*
Varietal Denomination: Orange Xenox

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 6 days.

(21) Appl. No.: 12/931,676

(22) Filed: Feb. 7, 2011

(51) Int. Cl.
*A01H 5/00* (2006.01)

(52) U.S. Cl. ..... Plt./479

(58) Field of Classification Search ..... Plt./479
See application file for complete search history.

*Primary Examiner* — Susan McCormick Ewoldt
(74) *Attorney, Agent, or Firm* — C. A. Whealy

(57) ABSTRACT

A new and distinct cultivar of Sedum plant named 'Orange Xenox', characterized by its upright plant habit; basally branching habit; dense and bushy growth habit; greyed purple to brown-colored leaves; numerous orange-colored flowers; and good garden performance.

2 Drawing Sheets

Botanical designation: *Hylotelephium spectabile.*
Cultivar denomination: 'ORANGE XENOX'.

BACKGROUND OF THE INVENTION

The present invention relates to a new and distinct cultivar of Sedum plant, botanically known as *Hylotelephium spectabile* and hereinafter referred to by the name 'Orange Xenox'.

The new Sedum plant is a product of a planned breeding program conducted by the Inventor in Rijpwetering, The Netherlands. The objective of the breeding program is to create new strong and healthy Sedum plants with numerous attractive flowers.

The new Sedum plant originated from a cross-pollination during the summer of 2007 in Rijpwetering, The Netherlands, *of Hylotelephium spectabile* 'Xenox', disclosed in U.S. Plant Pat. No. 16,888, as the female, or seed, parent with *Hylotelephium spectabile* 'Sunkissed', disclosed in U.S. Plant Pat. No. 16,927, as the male, or pollen, parent. The new Sedum plant was discovered and selected by the Inventor as a single flowering plant within the progeny of the stated cross-pollination in a controlled greenhouse environment in Rijpwetering, The Netherlands during the summer of 2008.

Asexual reproduction of the new Sedum plant by vegetative cuttings in a controlled environment in Rijpwetering, The Netherlands since the summer of 2008, has shown that the unique features of this new Sedum plant are stable and reproduced true to type in successive generations.

SUMMARY OF THE INVENTION

Plants of the new Sedum have not been observed under all possible environmental conditions. The phenotype may vary somewhat with variations in environment such as temperature and light intensity without, however, any variance in genotype.

The following traits have been repeatedly observed and are determined to be the unique characteristics of 'Orange Xenox'. These characteristics in combination distinguish 'Orange Xenox' as a new and distinct Sedum plant:

1. Upright plant habit.
2. Basally branching habit; dense and bushy growth habit.

3. Greyed purple to brown-colored leaves.
4. Numerous orange-colored flowers.
5. Good garden performance.

Plants of the new Sedum differ from plants of the female parent, 'Xenox', primarily in flower color as plants of 'Xenox' have orange white to greyed yellow-colored flowers. In addition, plants of the new Sedum have darker-colored leaves than plants of 'Xenox'.

Plants of the new Sedum differ from plants of the male parent, 'Sunkissed', primarily in flower color as plants of 'Sunkissed' have yellow-colored flowers. In addition, plants of the new Sedum and 'Sunkissed' differ in leaf color.

Plants of the new Sedum can also be compared to plants of *Hylotelephium spectabile* 'Yellow Xenox', disclosed in U.S. Plant Pat. No. 21,528. Plants of the new Sedum and 'Yellow Xenox' differ primarily in flower color as plants of 'Yellow Xenox' have yellow-colored flowers. In addition, plants of the new Sedum and 'Yellow Xenox' differ in leaf color.

BRIEF DESCRIPTION OF THE PHOTOGRAPHS

The accompanying colored photographs illustrate the overall appearance of the new Sedum plant showing the colors as true as it is reasonably possible to obtain in colored reproductions of this type. Colors in the photographs may differ slightly from the color values cited in the detailed botanical description which accurately describe the colors of the new Sedum plant.

The photograph on the first sheet comprises a side perspective view of typical flowering plants of 'Orange Xenox' grown in a ground bed.

The photograph at the top of the second sheet is a close-up view of typical inflorescences of 'Orange Xenox'.

The photograph at the bottom of the second sheet is a close-up view of a typical plant of 'Orange Xenox'.

DETAILED BOTANICAL DESCRIPTION

The aforementioned photographs and following observations, measurements and values describe plants grown during the late summer in ground beds in an outdoor nursery in Rijpwetering, The Netherlands and under commercial practice. During the production of the plants, day temperatures ranged from 12° C. to 32° C. and night temperatures ranged from 6° C. to 18° C. Plants were two years old when the photographs and description were taken. In the following description, color references are made to The Royal Horticultural Society Colour Chart, 2007 Edition, except where general terms of ordinary dictionary significance are used.

Botanical classification: *Hylotelephium spectabile* 'Orange Xenox'.

Parentage:

*Female, or seed, parent.*—*Hylotelephium spectabile* 'Xenox', disclosed in U.S. Plant Pat. No. 16,888.

*Male, or pollen, parent.*—*Hylotelephium spectabile* 'Sunkissed', disclosed in U.S. Plant Pat. No. 16,927.

Propagation:

*Type*.—By vegetative cuttings.

*Time to initiate roots, summer*.—About four weeks at 18° C.

*Time to produce a rooted young plant, summer*.—About three months at 18° C.

*Root description*.—Thick, fleshy; greyed white in color.

*Rooting habit*.—Moderately freely branching; medium in density.

Plant description:

*Plant form/habit*.—Herbaceous perennial; upright plant habit; narrow inverted triangle; moderately vigorous growth habit; freely basally branching habit with about four basal branches developing per plant; dense and bushy growth habit.

*Plant height*.—About 48.8 cm.

*Plant width* (*spread*).—About 29.1 cm.

*Lateral branches*.—Length: About 35 cm. Diameter: About 9 mm. Internode length: About 3.3 cm. Strength: Strong. Texture: Smooth, glabrous. Color: Close to 183C to 183D; towards the base, close to 144B to 144C.

Foliage description:

*Arrangement*.—Opposite, simple; sessile.

*Length*.—About 6.4 cm.

*Width*.—About 3.8 cm.

*Shape*.—Ovate.

*Apex*.—Bluntly acute.

*Base*.—Cordate.

*Margin*.—Irregularly and shallowly dentate.

*Texture, upper and lower surfaces*.—Smooth, glabrous; succulent.

*Venation pattern*.—Pinnate.

*Color*.—Developing leaves, upper surface: Close to N137C and 147A. Developing leaves, lower surface: Close to 147B. Fully expanded leaves, upper surface: Close to N186C and 200A to 200B; venation, close to N186C. Fully expanded leaves, lower surface: Close to 137B to 137C; venation, close to 144C, towards the base, tinged with close to 181A.

Flower description:

*Flower type/habit*.—Small rotate flowers arranged in terminal compound cymes; flowers face upright to slightly outward; freely flowering habit with about 2,800 flower buds and flowers developing per plant.

*Fragrance*.—Faint, nectar-like.

*Natural flowering season*.—Plants begin flowering about nine months after planting; in the garden, plants flower continuously flowering during August and September in The Netherlands.

*Postproduction longevity*.—Flowers last about two weeks on the plant; flowers persistent.

*Flower buds*.—Height: About 5 mm. Diameter: About 3.5 mm. Shape: Broadly elliptic. Color: Close to 179A to 179B; towards the base, close to 182D.

*Inflorescence height*.—About 11.8 cm.

*Inflorescence diameter*.—About 12.3 cm.

*Flower diameter*.—About 8 mm.

*Flower depth*.—About 6 mm.

*Petals*.—Quantity per flower: Typically five in a single whorl; petals fused at the base. Length: About 5 mm. Lobe width: About 2 mm. Shape: Ovate. Apex: Acute. Margin: Entire. Texture, upper and lower surfaces: Smooth, glabrous. Color: When opening and fully opened, upper surface: Close to 159A to 159B; center, tinged with close to 185D. When opening and fully opened, lower surface: Close to 184C; center, close to 159A to 159B tinged with close to 185D; towards the base, close to 155C.

*Sepals*.—Quantity per flower: Typically five in a single whorl, fused at the base; calyx, campanulate. Length: About 1.5 mm. Width: About 0.75 mm. Shape: Narrowly ovate. Apex: Acute. Margin: Entire. Texture, upper and lower surfaces: Smooth, glabrous. Color: When opening, upper and lower surfaces: Close to 148A heavily tinged with close to 183A. Fully opened, upper and lower surfaces: Close to 148A heavily tinged with close to 183A.

*Peduncles*.—Length: About 9.9 cm. Diameter: About 3 mm. Angle: Erect to about 30° from vertical. Strength: Moderately strong. Texture: Smooth, glabrous. Color: Close to 183B tinged with close to 148A to 148B.

*Pedicels*.—Length: About 4 mm. Diameter: About 0.75 mm. Angle: Erect to about 50° from vertical. Strength: Moderately strong. Texture: Smooth, glabrous. Color: Close to N186C.

*Reproductive organs*.—Stamens: Quantity per flower: Typically ten. Filament length: About 3 mm. Filament color: Close to 159A. Anther shape: Broadly oblong, flattened. Anther length: About 0.5 mm. Anther color: Close to 174A. Pollen amount: Scarce. Pollen color: Close to 5B to 5C. Pistils: Quantity per flower: Typically five. Pistil length: About 4 mm. Stigma shape: Pointed. Stigma color: Close to 185A to 185B. Style length: About 3.5 mm. Style color: Close to 162C to 162D; color becoming closer to 184C and 184D with development. Ovary color: Close to 162C to 162D; color becoming closer to 184D and 185D with development.

*Seed/fruit*.—Seed and fruit development have not been observed.

Disease/pest resistance: Plants of the new Sedum have not been noted to be resistant to pathogens and pests common to Sedum.

Garden performance: Plants of the new Sedum have been observed to have good garden performance and to tolerate rain and wind; plants of the new Sedum tolerate high temperatures of about 35° C. and are winter hardy to USDA Hardiness Zone 5.

It is claimed:

1. A new and distinct Sedum plant named 'Orange Xenox' as illustrated and described.

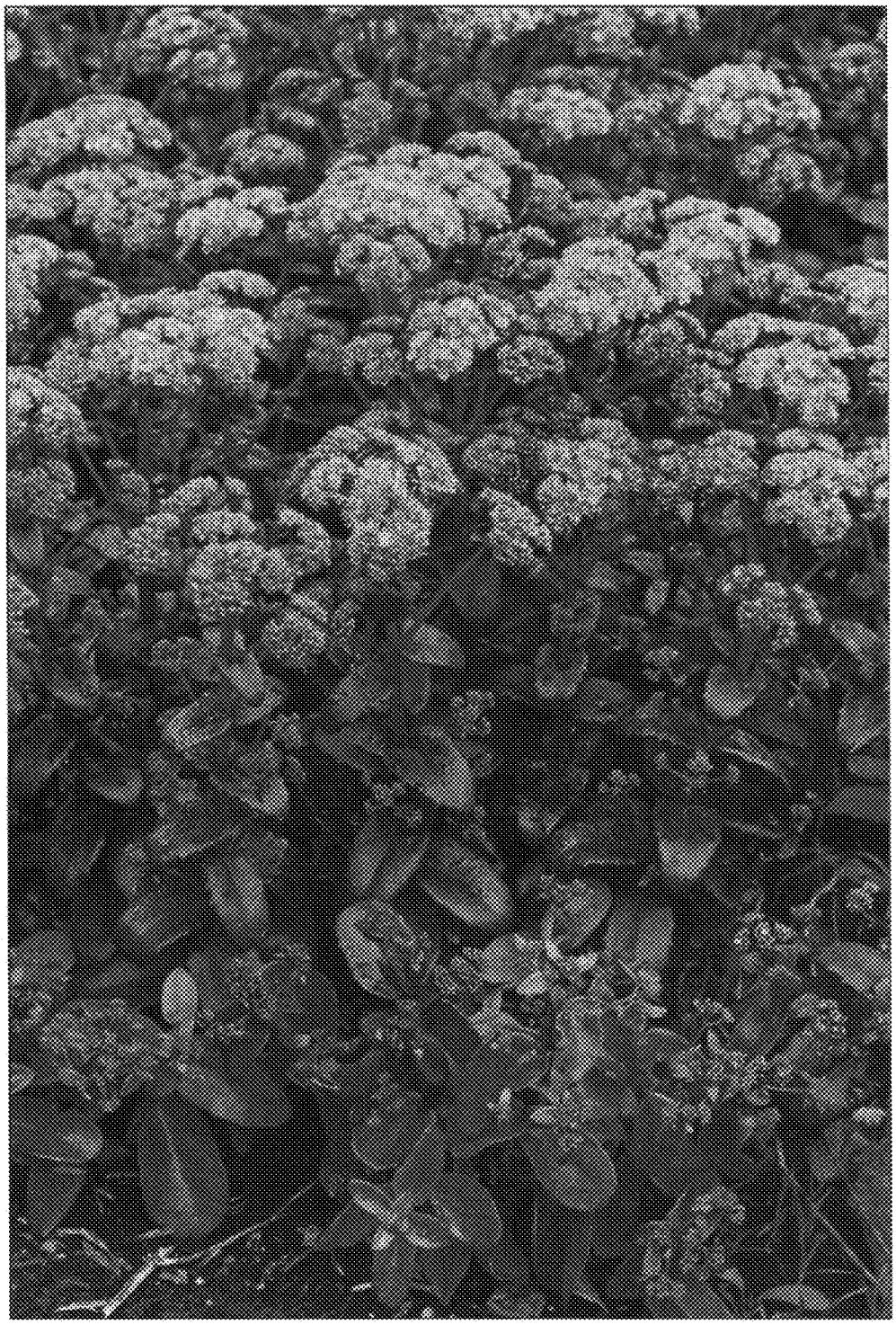

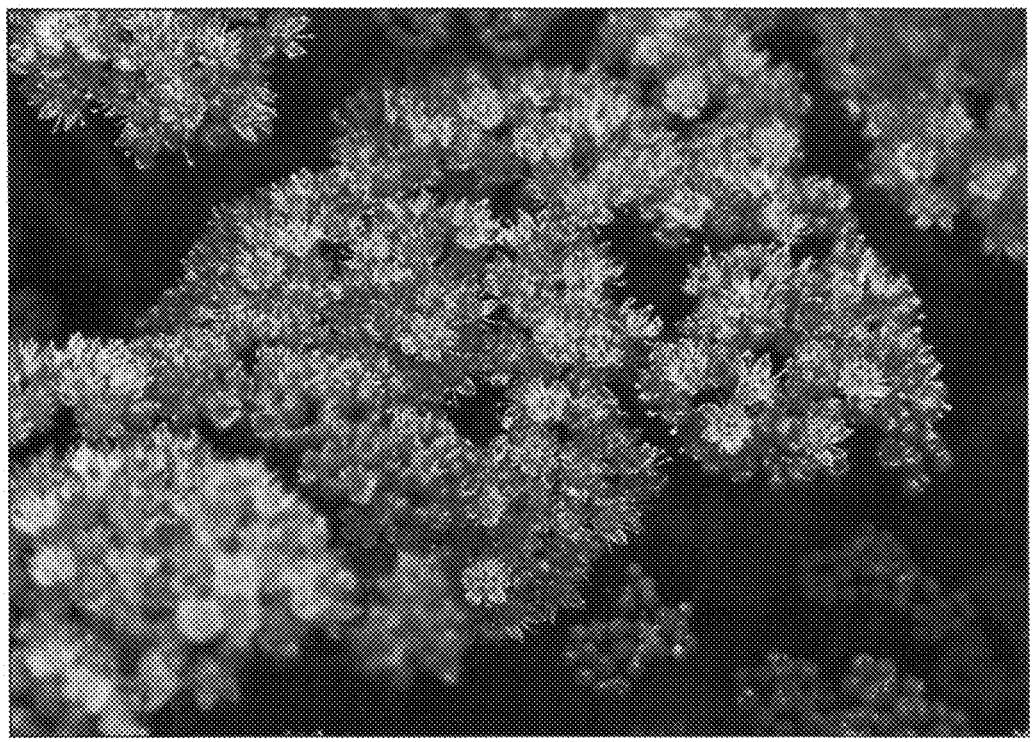
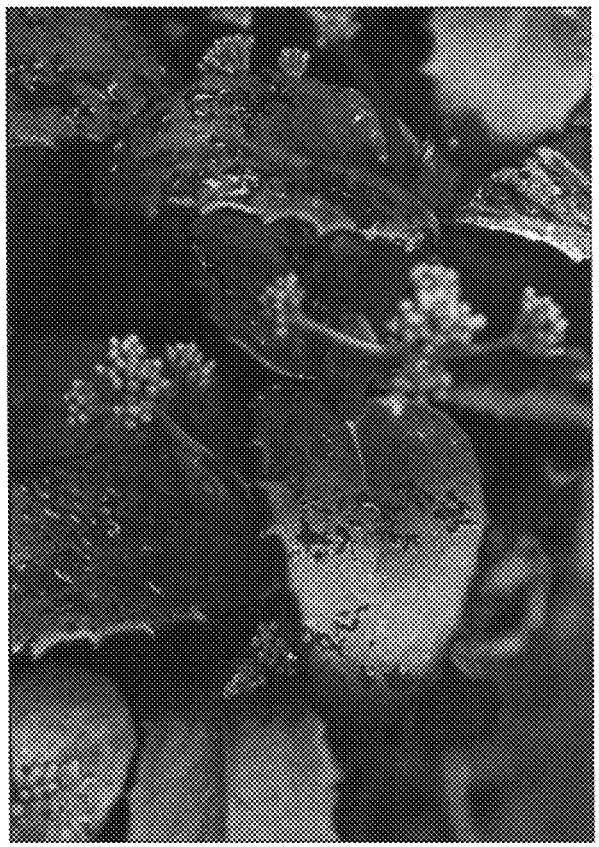

* * * * *